(12) United States Patent
Barbera et al.

(10) Patent No.: US 7,727,556 B2
(45) Date of Patent: Jun. 1, 2010

(54) SOLUBILITY OF HYDROPHOBIC DRUGS WITH A COMPOUND HAVING A CARBOXYLIC ACID MOIETY

(75) Inventors: Gary Barbera, Medford, NJ (US); Chetan Chhabildas Doshi, Plainsboro, NJ (US); Mahendra R Patel, East Brunswick, NJ (US); Pablo Davila, East Windsor, NJ (US); Satishkumar Ambalal Patel, West Windsor, NJ (US)

(73) Assignee: Sandoz AG, Basel (CH)

( * ) Notice: Subject to any disclaimer, the term of this patent is extended or adjusted under 35 U.S.C. 154(b) by 765 days.

(21) Appl. No.: 11/124,343

(22) Filed: May 6, 2005

(65) Prior Publication Data
US 2005/0249814 A1    Nov. 10, 2005

Related U.S. Application Data

(60) Provisional application No. 60/568,712, filed on May 6, 2004.

(51) Int. Cl.
*A61K 9/14*    (2006.01)
(52) U.S. Cl. ..................................................... 424/489
(58) Field of Classification Search ................. 424/489; 514/247, 254; *A61K 31/495*
See application file for complete search history.

(56) References Cited

U.S. PATENT DOCUMENTS

| | | | |
|---|---|---|---|
| 4,732,915 A | 3/1988 | Ayer et al. | |
| 4,831,031 A | 5/1989 | Lowe, III et al. | 514/254 |
| 5,312,925 A | 5/1994 | Allen et al. | 544/368 |
| 5,364,646 A | 11/1994 | Gruber et al. | |
| 6,150,366 A | 11/2000 | Arenson et al. | 514/253 |
| 6,497,899 B2 | 12/2002 | Thombre et al. | 424/464 |
| 6,541,513 B2 | 4/2003 | Plata-Salaman et al. | 514/483 |
| 6,548,555 B1 | 4/2003 | Curatolo et al. | 514/772.4 |
| 6,894,042 B2 | 5/2005 | Walker et al. | 514/212.05 |
| 6,911,543 B2 | 6/2005 | Walker et al. | 546/80 |
| 2002/0004504 A1* | 1/2002 | Howard | 514/247 |

FOREIGN PATENT DOCUMENTS

| | | | |
|---|---|---|---|
| EP | 0 965 343 | * | 12/1999 |
| EP | 0 965 343 A2 | * | 12/1999 |
| EP | 0965343 | | 12/1999 |
| WO | WO97/41896 | | 11/1997 |
| WO | WO9820873 | | 5/1998 |
| WO | WO0072847 | | 12/2000 |
| WO | WO2004/039410 | | 5/2004 |
| WO | WO2004/039411 | | 5/2004 |
| WO | WO 2005/061493 | * | 7/2005 |
| WO | WO2005107719 | | 11/2005 |

OTHER PUBLICATIONS

Derwent Accession No. 2006-585625.*
Written Opinion of the International Searching Authority.
Written Opinion of the International Searching Authority, Dated: Apr. 2006.

* cited by examiner

*Primary Examiner*—Robert A Wax
*Assistant Examiner*—Jeffrey T Palenik
(74) *Attorney, Agent, or Firm*—Luedeka, Neely & Graham, P.C.

(57) ABSTRACT

A pharmaceutical composition having improved solubility comprising a hydrophobic drug or pharmaceutically acceptable salt thereof and a compound having at least one carboxylic acid moiety, wherein the molar ratio of the compound having at least one carboxylic acid moiety to the hydrophobic drug or pharmaceutically acceptable salt thereof is from about 0.1:1 to about 25:1. The pharmaceutical composition exhibits rapid dissolution upon contact with physiological solvents, such as water, saliva or gastrointestinal fluids.

30 Claims, 1 Drawing Sheet

SOLUBILITY OF HYDROPHOBIC DRUGS WITH A COMPOUND HAVING A CARBOXYLIC ACID MOIETY

This application claims benefit to U.S. Provisional Application No. 60/568,712, filed May 6, 2004, the entire disclosure of which is hereby incorporated by reference.

FIELD OF THE INVENTION

The present invention provides a pharmaceutical composition having improved solubility comprising a hydrophobic drug or pharmaceutically acceptable salt thereof and a compound having at least one carboxylic acid moiety, wherein the molar ratio of the compound having at least one carboxylic acid moiety to the hydrophobic drug or pharmaceutically acceptable salt thereof is from about 0.1:1 to about 25:1.

BACKGROUND OF THE INVENTION

Hydrophobic drugs, i.e., drugs having poor solubility in aqueous solution, present difficult formulation problems for effective administration to patients. A well-designed formulation must, at a minimum, be capable of presenting a therapeutically-effective amount of the hydrophobic drug to the desired absorption site, in an absorbable form. Even this minimal functionality is difficult to achieve with hydrophobic drugs because of the slow disintegration or dissolution. Especially in intestinal fluid, a drug that does not dissolve sufficiently cannot pass via the intestinal wall membrane into the bloodstream, and is simply excreted by the individual via their intestinal tract without providing a therapeutic benefit.

An example of a hydrophobic drug is ziprasidone, also known as 5-[2-[4-(1,2-benzisothiazol-3-yl)-1-piperazinyl]ethyl]-6-chloro-1,3-dihydro-2H-indol-2-one. Ziprasidone is described in U.S. Pat. Nos. 4,831,031 and 5,312,925. Ziprasidone is an antipsychotic drug indicated for the treatment of schizophrenia. The empirical formula of $C_{21}H_{21}ClN_4OS$ (free base of ziprasidone) has the following structural formula:

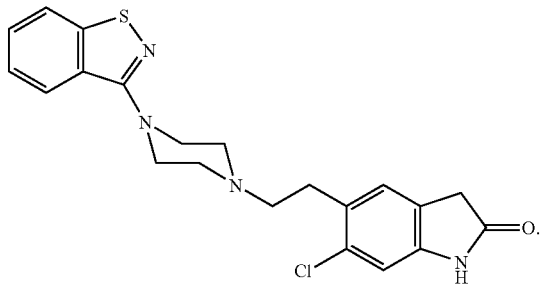

Ziprasidone capsules contain a monohydrochloride, monohydrate salt of ziprasidone. Chemically, ziprasidone hydrochloride (HCl) monohydrate is 5-[2-[4-(1,2-benzisothiazol-3-yl)-1-piperazinyl]ethyl]-6-chloro-1,3-dihydro-2H-indol-2-one, monohydrochloride, monohydrate. The empirical formula is $C_{21}H_{21}ClN_4OS$ HCL $H_2O$. Ziprasidone capsules are commercially-available from Pfizer under the trademark Geodon® capsules and contain ziprasidone HCl monohydrate, lactose, pre-gelatinized starch and magnesium stearate.

U.S. Pat. No. 6,150,366 describes compositions containing crystalline ziprasidone free base or crystalline ziprasidone HCl particles having a mean particle size equal to or less than about 85 microns and a pharmaceutically acceptable diluent or carrier.

It would be desirable to improve the solubility of hydrophobic drug containing compositions without necessarily employing such conventional methods as milling or micronizing the drug in order to increase solubility.

SUMMARY OF THE INVENTION

The invention provides a pharmaceutical composition having improved solubility comprising a hydrophobic drug or pharmaceutically acceptable salt thereof and a compound having at least one carboxylic acid moiety, wherein the molar ratio of the compound having at least one carboxylic acid moiety to the hydrophobic drug or pharmaceutically acceptable salt thereof is from about 0.1:1 to about 25:1.

According to another aspect, the invention provides a method for treating schizophrenia in a patient comprising administering an effective amount of a pharmaceutical composition to said patient, said composition comprising ziprasidone hydrochloride anhydrous and a compound having at least one carboxylic acid moiety, wherein the molar ratio of the compound having at least one carboxylic acid moiety to the ziprasidone hydrochloride anhydrous is from about 0.1:1 to about 25:1.

According to another aspect, the invention provides a wet granulation method of preparing a pharmaceutical composition having improved solubility comprising a hydrophobic drug or pharmaceutically acceptable salt thereof and a compound having at least one carboxylic acid moiety, wherein the molar ratio of the compound having at least one carboxylic acid moiety to the hydrophobic drug or pharmaceutically acceptable salt thereof is from about 0.1:1 to about 25:1, said method comprising:
  (a) combining a compound having at least one carboxylic acid moiety with a hydrophobic drug or pharmaceutically acceptable salt thereof, and optionally one or more excipients, to form a premix;
  (b) adding a solvent, and optionally a surfactant, to the premix formed in Step (a) to form a wet granulation; and
  (c) drying the wet granulation to form a pharmaceutical composition.

According to another aspect, the invention provides a dry compaction method of preparing a pharmaceutical composition having improved solubility comprising a hydrophobic drug or pharmaceutically acceptable salt thereof and a compound having at least one carboxylic acid moiety, wherein the molar ratio of the compound having at least one carboxylic acid moiety to the hydrophobic drug or pharmaceutically acceptable salt thereof is from about 0.1:1 to about 25:1, said method comprising:
  (a)" combining a compound having at least one carboxylic acid moiety with a hydrophobic drug or pharmaceutically acceptable salt thereof, and optionally one or more excipients, to form a premix;
  (b)" compacting the premix formed in Step (a)", optionally in the presence of one or more excipients, to form an agglomerate; and
  (c)" breaking the agglomerate formed in Step (b)", optionally in the presence of one or more excipients, to form a pharmaceutical composition.

The pharmaceutical composition of the invention exhibit rapid dissolution upon contact with physiological solvents, such as water, saliva or gastrointestinal fluids, due to the presence of a compound having at least one carboxylic acid moiety, as compared to commercially-available ziprasidone capsules.

DESCRIPTION OF THE INVENTION

Figure 1:
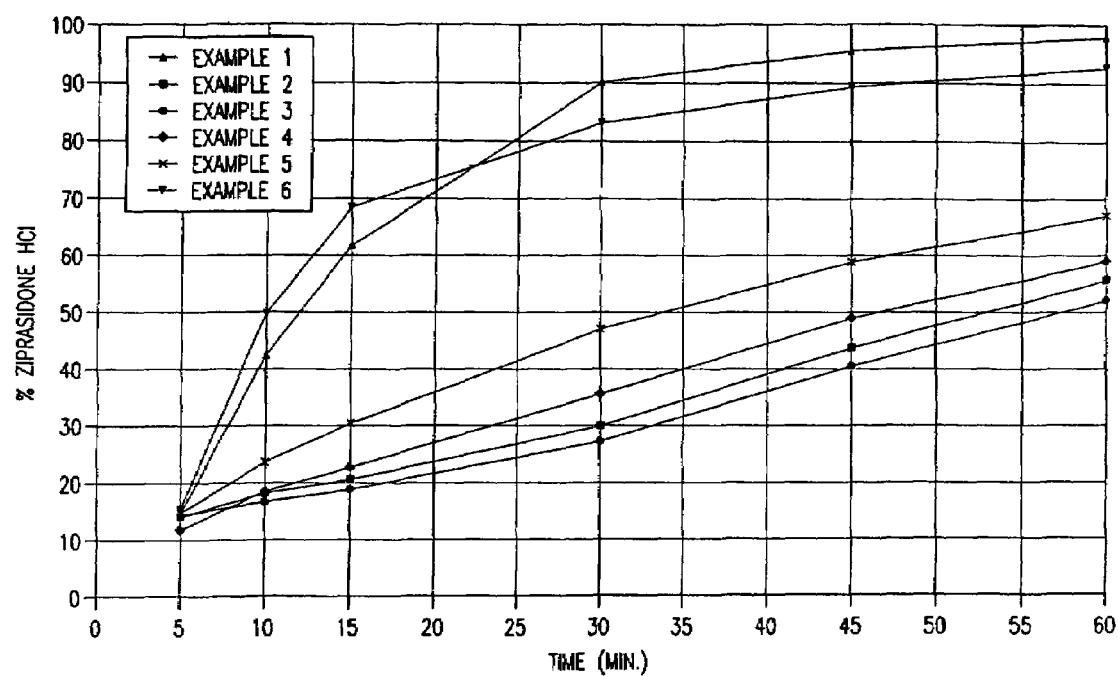
FIG. 1 is a dissolution profile comparing four ziprasidone HCl anhydrous capsules prepared with a compound having at least one carboxylic acid moiety to a ziprasidone HCl anhydrous capsule prepared without a compound having at least one carboxylic acid moiety, and a commercially available ziprasidone HCl monohydrate capsule (Geodon® capsule).

The pharmaceutical compositions of the invention comprises a hydrophobic drug or pharmaceutically acceptable salt thereof and a compound having at least one carboxylic acid moiety, wherein the molar ratio of the compound having at least one carboxylic acid moiety to hydrophobic drug or pharmaceutically acceptable salt thereof is from about 0.1:1 to about 25:1. Examples of hydrophobic drugs include, but are not limited to, ziprasidone, raloxifene, paroxetine, glimepiride, anagrelide, modafinil, paroxetine, cabergoline, replaginide, glipizide, benzodiazepines, clofibrate, chlorpheniramine, dinitirate, digoxin, digitoxin, ergotamin tartate, estradiol, fenofibrate, griseofulvin, hydrochlorothiazide, hydrocortisone, isosorbide, medrogeston, oxyphenbutazone, prednisolone, prednisone, polythiazide, progensterone, spironolactone, tolbutamide, 10,11-dihydro-5H-dibenzo[a, d]cyclo-heptene-5-carboxamide, 5H-dibenzo[a,d]cycloheptene-5-carboxamide and the like, including pharmaceutically acceptable salts thereof. A mixture of hydrophobic drugs may also be used. The hydrophobic drug may be crystalline, semi-crystalline or amorphous. While the invention is illustrated with particularly hydrophobic drugs, the pharmaceutical composition of the invention is also applicable to more soluble drugs in need of enhanced dissolution and bioavailability.

The term "pharmaceutically acceptable salt" refers to those salts of the above described drugs that are not substantially toxic at the dosage administered to achieve the desired effect and do not independently possess significant pharmacological activity. The salts included within the scope of this term are pharmaceutically acceptable acid addition salts of a suitable inorganic or organic acid. Suitable inorganic acids are, e.g., hydrochloric, hydrobromic, sulfuric and phosphoric acids. Suitable organic acids include carboxylic acids, such as acetic, propionic, glycolic, lactic, pyruvic, malonic, succinic, fumaric, malic, tartaric, citric, cyclamic, ascorbic, maleic, hydroxymaleic, dihydroxymaleic, benzoic, phenylacetic, 4-aminobenzoic, 4-hydroxybenzoic, anthranillic, cinnamic, salicylic, 4-aminosalicyclic, 2-phenoxybenzoic, 2-acetoxybenzoic and mandelic acid; sulfonic acids, such as methanesulfonic, ethanesulfonic and β-hydroxyethanesulfonic acid. In addition, "pharmaceutically acceptable salts" include those salts of the above described drugs formed with inorganic and organic bases, such as those of alkali metals, e.g., sodium, potassium and lithium; alkaline earth metals, e.g., calcium and magnesium; light metals of group IIIA, e.g., aluminum; organic amines, e.g., primary, secondary or tertiary amines, such as cyclohexylamine, ethylamine, pyridine, methylaminoethanol and piperazine. The salts are prepared by conventional means by one of ordinary skill in the art as, e.g., by treating the drug compound with an appropriate acid or base. Such salts can exist in either a hydrated or anhydrous form. Preferably, the hydrophobic drug is crystalline ziprasidone HCl anhydrous.

The ziprasidone HCl anhydrous is preferably in the form of particles having a mean particle size of greater than 85 microns, more preferably from about 100 microns to about 150 microns. Most preferably, the particles have a mean particle size from about 120 microns to about 140 microns, e.g., 135 microns.

The amount of hydrophobic drug or pharmaceutically acceptable salt thereof in the pharmaceutical compositions is preferably from about 0.1 mg to about 2000 mg. More preferably, the amount of hydrophobic drug or pharmaceutically acceptable salt thereof in the pharmaceutical compositions is from about 20 mg to about 200 mg.

The compound having at least one carboxylic acid moiety is preferably selected from monocarboxylic acids, dicarboxylic acids, tricarboxylic acids, tetracarboxylic acids, pentacarboxylic acids and polymers having at least one carboxylic acid group. A mixture of compounds having at least one carboxylic acid moiety may also be used. Specific examples of compounds having at least one carboxylic acid moiety include: ascorbic acid, maleic acid, citric acid succinic acid, glutaric acid, adipic acid, azelaic acid, sebacic acid, fumaric acid, maleic acid, itaconic acid, 1,3-cyclohexane dicarboxylic acid, 1,4-cyclohexanedicarboxylic acid, diglycolic acid, 2,5-norbornanedicarboxylic acid, phthalic acid, terephthalic acid, 1,4-naphthalenedicarboxylic acid, 2,5-naphthalenedicarboxylic acid, diphenic acid, 4,4'-oxydibenzoic acid, 4,4'-sulfonyldibenzoic acid, isophthalic acid and polymethylmethacrylate, polyacrylic acid, glucoronic acid, manuronic acid and alginic acid. More preferably, the compound having at least one carboxylic acid moiety is selected from ascorbic acid, maleic acid or citric acid. Most preferably, the compound having at least one carboxylic acid moiety is citric acid.

The molar ratio of the compound having at least one carboxylic acid moiety to hydrophobic drug or pharmaceutically acceptable salt thereof is from about 0.1:1 to about 25:1. Preferably, the molar ratio of the compound having at least one carboxylic acid moiety to hydrophobic drug or pharmaceutically acceptable salt thereof is from about 1:1 to about 15:1. More preferably, the molar ratio of the compound having at least one carboxylic acid moiety to hydrophobic drug or pharmaceutically acceptable salt thereof is from about 2:1 to about 10:1, most preferably the molar ratio is about 3.5:1 to about 4:1.

It is within the scope of the invention for the pharmaceutical compositions, in addition to the hydrophobic drug or pharmaceutically acceptable salt thereof and compound having at least one carboxylic acid moiety, to include one or more pharmaceutically acceptable excipients. Examples of such excipients are enteric-coating agents, diluents, binders, anti-caking agents, amino acids, fibers, solubilizers, disintegrants, fillers, lubricants, emulsifiers, surfactants, flavorants, solvents, buffers, stabilizers, colorants, dyes, anti-oxidants, anti-adherents, preservatives, electrolytes, glidants and carrier materials. A combination of excipients may also be used. Such excipients are known to those skilled in the art, and thus, only a limited number will be specifically referenced.

Preferred binders include, but are not limited to, starches, e.g., potato starch, wheat starch, corn starch, pre-gelatinized starch; gums, such as gum tragacanth, acacia gum and gelatin; and polyvinyl pyrrolidone, e.g., Povidone. More preferably, the binder is pre-gelatinized starch.

Preferred fillers include, but are not limited to, microcrystalline cellulose, starch, pre-gelatinized starch, modified starch, dibasic calcium phosphate dihydrate, calcium sulfate trihydrate, calcium sulfate dihydrate, calcium carbonate, dextrose, sucrose, lactose, mannitol and sorbitol. More preferably, the filler is lactose.

Examples of disintegrants include:
1) Natural starches, such as maize starch, potato starch and the like, directly compressible starches, e.g., Sta-rx® 1500; modified starches, e.g., carboxymethyl starches and sodium starch glycolate, available as Primojel®, Explotab®, Explosol®; and starch derivatives, such as amylase.
2) Cross-linked polyvinylpyrrolidones, e.g., crospovidones, such as Polyplasdone® XL and Kollidon® CL.
3) Alginic acid and sodium alginate.
4) Methacrylic acid-divinylbenzene co-polymer salts, e.g., Amberlite® IRP-88.
5) Cross-linked sodium carboxymethylcellulose, available as, e.g., Ac-di-sol®, Primellose®, Pharmacel® XL, Explocel® and Nymcel® ZSX.

Additional disintegrants also include hydroxypropyl cellulose, hydroxypropylmethyl cellulose, croscarmellose sodium, sodium starch glycolate, polacrillin potassium, polyacrylates, such as Carbopol®, magnesium aluminium silicate and bentonite.

Examples of surfactants include:
1) Reaction products of a natural or hydrogenated castor oil and ethylene oxide. The polyethyleneglycol-hydrogenated castor oils available under the trademark CREMOPHOR are especially suitable, such as CREMOPHOR RH 40 and CREMOPHOR RH 60. Also suitable are polyethyleneglycol castor oils, such as that available under the trade name CREMOPHOR EL;
2) Polyoxyethylene-sorbitan-fatty acid esters, also called polysorbates, e.g., mono- and tri-lauryl, palmityl, stearyl and oleyl esters of the type known and commercially-available under the trademark TWEEN:
   20 [polyoxyethylene(20)sorbitanmonolaurate],
   21 [polyoxyethylene(4)sorbitanmonolaurate],
   40 [polyoxyethylene(20)sorbitanmonopalmitate],
   60 [polyoxyethylene(20)sorbitanmonostearate],
   65 [polyoxyethylene(20)sorbitantristearate],
   80 [polyoxyethylene(20)sorbitanmonooleate],
   81 [polyoxyethylene(5)sorbitanmonooleate] and
   85 [polyoxyethylene(20)sorbitantrioleate].
   A preferred product of this class is TWEEN 80.
   Although polyethylene glycol (PEG) itself does not function as a surfactant, a variety of PEG-fatty acid esters have useful surfactant properties. Among the PEG-fatty acid monoesters, esters of lauric acid, oleic acid and stearic acid are most useful. Among the surfactants of Table 1, preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate.
3) Polyoxyethylene fatty acid esters, for example polyoxyethylene stearic acid esters of the type known and commercially available under the trademark MYRJ.
4) Polyoxyethylene-polyoxypropylene co-polymers and block co-polymers, e.g., of the type known and commercially-available under the trademark PLURONIC, EMKALYX and POLOXAMER. Preferred products of this class are PLURONIC F68 and POLOXAMER 188.
5) Dioctylsulfosuccinate or di-[2-ethylhexyl]-succinate.
6) Phospholipids, in particular, lecithins. Suitable lecithins include, in particular, soybean lecithins.
7) Propylene glycol mono- and di-fatty acid esters, such as propylene glycol dicaprylate (also known and commercially-available under the trademark MIGLYOL 840), propylene glycol dilaurate, propylene glycol hydroxystearate, propylene glycol isostearate, propylene glycol laurate, propylene glycol ricinoleate and propylene glycol stearate.
8) Polyoxyethylene alkyl ethers, such as those commercially-available under the trademark BRIJ, e.g., BRIJ 92V and BRIJ 35.
9) Tocopherol esters, e.g., tocopheryl acetate and tocopheryl acid succinate.
10) Docusate salts, e.g., dioctylsulfosuccinate or related compounds, such as di-[2-ethylhexyl]-succinate.

Preferred diluents include, but are not limited to, dextrose, sorbitol, sucrose, lactose, mannitol, urea, potassium chloride, sodium chloride, gelatin, starch, methyl cellulose, ethyl cellulose, propyl cellulose, hydroxymethyl cellulose, hydroxyethyl cellulose, hydroxypropyl cellulose, hydroxypropyl methyl cellulose, silica, polyvinyl alcohol, polyvinylpyrrolidone and magnesium stearate.

In one embodiment of the invention, the pharmaceutical composition of the invention is prepared by a wet granulation method comprising:
   (a) combining a compound having at least one carboxylic acid moiety with a hydrophobic drug or pharmaceutically acceptable salt thereof, and optionally one or more excipients, to form a premix;
   (b) adding a solvent, and optionally a surfactant, to the premix formed in Step (a) to form a wet granulation; and
   (c) drying the wet granulation to form a pharmaceutical composition.

In another embodiment of the invention, the pharmaceutical composition of the invention is prepared by a wet granulation method comprising:
   (a)' combining a hydrophobic drug or pharmaceutically acceptable salt thereof and optionally one or more excipients to form a premix;
   (b)' adding a mixture comprising a solvent and a compound having at least one carboxylic acid moiety to the premix formed in Step (a)' to form a wet granulation; and
   (c)' drying the wet granulation to form a pharmaceutical composition.

Drying techniques useful for drying the granulation include spray-drying, flash drying, ring drying, micron drying, tray drying, vacuum drying, radio-frequency drying, microwave drying and lyophilizing.

In another embodiment of the invention, the pharmaceutical composition of the invention is prepared by a dry compaction method comprising:
   (a)" combining a compound having at least one carboxylic acid moiety with a hydrophobic drug or pharmaceutically acceptable salt thereof, and optionally one or more excipients, to form a premix;
   (b)" compacting the premix formed in Step (a)", optionally in the presence of one or more excipients, to form an agglomerate; and
   (c)" breaking the agglomerate formed in Step (b)", optionally in the presence of one or more excipients, to form a pharmaceutical composition.

In the dry compaction method, compacting in Step (b)" is preferably accomplished by a mini-press or roller compactor. A preferred roller compactor is a Gerdis roller compactor.

In the dry compaction method, breaking in Step (c)" is preferably accomplished by means of a mill. Useful mills include fluid energy mill, ball mill or rod mill, hammer mill, cutting mill and oscillating granulator. More specifically, suitable mills include, Quadro Comill, Fryma, Glatt Quick Sieve, Fluidaire, Fitzpatrick (Fitz mill), BTS mill and Tornado. A preferred mill is a Fitz mill.

The pharmaceutical compositions of the invention may be in the form of a capsule, caplet, powder, disc or tablet. In one embodiment of the invention, the compositions of the invention are enclosed inside a capsule, e.g., a gelatin capsule. For this, any gelatin capsule conventionally employed in the pharmaceutical formulation field can be used, such as the hard gelatin capsule or a HPMC capsule, such as Vegicap®.

The pharmaceutical compositions may comprise therapeutically effective amounts of the hydrophobic drug or pharmaceutically acceptable salt thereof.

The pharmaceutical compositions of the invention may be used as a medicament. Additionally, the pharmaceutical compositions of the invention may be used for the manufacture of a medicament.

In case the pharmaceutical composition of the invention comprises ziprasidone HCl as hydrophobic drug or a pharmaceutically acceptable salt thereof, said composition may be used for the treatment of psychotic disorders in a mammal, e.g. in a human patient, such as for the treatment of a neuroleptic disease, e.g. schizophrenia. Said treatment may be effected by administering the pharmaceutical composition according to the invention comprising a therapeutically effective amount of ziprasidone HCl to a human patient in need thereof.

In case the pharmaceutical composition of the invention comprises ziprasidone HCl as hydrophobic drug or a pharmaceutically acceptable salt thereof, said composition may be used for the manufacture of a medicament for the treatment of psychotic disorders in a mammal, e.g. in a human patient, such as for the treatment of a neuroleptic disease, e.g., schizophrenia.

The following non-limiting examples illustrate further aspects of the invention.

EXAMPLE 1

Comparative

Dissolution Study Using Ziprasidone HCl Monohydrate Capsules (Geodon® Capsules).

A USP Dissolution Apparatus 2 (paddle) was used at 75 rpm containing 900 mL of 0.05 M sodium phosphate monobasic anhydrous buffer containing 2% sodium lauryl sulphate, at pH 7.5 at approximately 37° C. Individually, three Geodon® capsules each containing ziprasidone HCl monohydrate (20 mg ziprasidone base), lactose, pre-gelatinized starch and magnesium stearate were evaluated and the average percent dissolution of ziprasidone HCl was plotted. The test results are summarized in Table 1 and FIG. 1.

EXAMPLE 2

Comparative

Preparation of Ziprasidone HCL Anhydrous Capsules without a Compound having at Least One Carboxylic Acid Moiety.

| Ingredient | Wt. % Composition | mg/Unit |
|---|---|---|
| Ziprasidone HCl Anhydrous | 29.03 | 21.77* |
| Lactose DT Anhydrous | 66.30 | 49.73 |
| Pre-gelatinized Starch | 4.0 | 3.0 |
| Magnesium Stearate | 0.67 | 0.5 |
| Total | 100.0 | 75.0 |

*21.77 mg ziprasidone HCl anhydrous equivalent to 20 mg of ziprasidone free base.

Ziprasidone HCl anhydrous having a mean particle size of 135 microns and lactose were mixed in a 250 mL beaker for 5 minutes using a spatula. Pre-gelatinized starch was added to the mixture and mixed for 5 minutes. Magnesium stearate was added to the mixture and mixed for 1 minute. The resulting blend was filled into size 4 hard gelatin capsules.

The ziprasidone capsules prepared in Example 2 were evaluated in a dissolution study as set forth in Example 1. The test results are summarized in Table 1 and FIG. 1.

EXAMPLE 3

Preparation of Ziprasidone HCl Anhydrous Capsules with 1 M Citric Acid.

| Ingredient | Wt. % Composition | mg/Unit |
|---|---|---|
| Ziprasidone HCl Anhydrous | 29.02 | 21.77* |
| Citric Acid | 12.0 | 9.0 |
| Lactose DT Anhydrous | 54.31 | 40.73 |
| Pre-gelatinized Starch | 4.0 | 3.0 |
| Magnesium Stearate | 0.67 | 0.5 |
| Total | 100.0 | 75.0 |

*21.77 mg ziprasidone HCl anhydrous equivalent to 20 mg of ziprasidone free base.

Ziprasidone HCl anhydrous having a mean particle size of 135 microns and citric acid were mixed in a 250 mL beaker for 5 minutes using a spatlua. Lactose and pre-gelatinized starch were added to the mixture and mixed for 5 minutes. Magnesium stearate was added to the mixture and mixed for 1 minute. The resulting blend was filled into size 4 hard gelatin capsules.

The ziprasidone capsules were evaluated in a dissolution study as set forth in Example 1. The test results are summarized in Table 1 and FIG. 1.

EXAMPLE 4

Preparation of Ziprasidone HCl Anhydrous Capsules with 2 M Citric Acid.

| Ingredient | Wt. % Composition | Mg/unit |
|---|---|---|
| Ziprasidone HCl Anhydrous | 29.02 | 21.77* |
| Citric Acid | 24.0 | 18.0 |
| Lactose DT Anhydrous | 42.31 | 31.73 |
| Pre-gelatinized Starch | 4.0 | 3.0 |
| Magnesium Stearate | 0.67 | 0.5 |
| Total | 100.0 | 75.0 |

*21.77 mg ziprasidone HCl anhydrous equivalent to 20 mg of ziprasidone free base.

Ziprasidone capsules were prepared according to the procedure set forth in Example 3. The ziprasidone HCl anhydrous had a mean particle size of 135 microns. The ziprasidone capsules were evaluated in a dissolution study as set forth in Example 1. The test results are summarized in Table 1 and FIG. 1.

EXAMPLE 5

Preparation of Ziprasidone HCl Anhydrous Capsules with 3 M Citric Acid.

| Ingredient | Wt. % Composition | Mg/unit |
|---|---|---|
| Ziprasidone HCl Anhydrous | 29.02 | 21.77* |
| Citric Acid | 36.0 | 27.0 |
| Lactose DT Anhydrous | 30.31 | 22.73 |
| Pre-gelatinized Starch | 4.0 | 3.0 |
| Magnesium Stearate | 0.67 | 0.5 |
| Total | 100.0 | 75.0 |

*21.77 mg ziprasidone HCl anhydrous equivalent to 20 mg of ziprasidone free base.

Ziprasidone capsules were prepared according to the procedure set forth in Example 3. The ziprasidone HCl anhydrous had a mean particle size of 135 microns. The ziprasidone capsules were evaluated in a dissolution study as set forth in Example 1. The test results are summarized in Table 1 and FIG. 1.

EXAMPLE 6

Preparation of Ziprasidone HCl Anhydrous Capsules with 5 M Citric Acid.

| Ingredient | Wt. % Composition | mg/Unit |
|---|---|---|
| Ziprasidone HCl Anhydrous | 25.61 | 21.77* |
| Citric Acid | 52.94 | 45.0 |
| Lactose DT Anhydrous | 11.45 | 9.73 |
| Pre-gelatinized Starch | 3.53 | 3.0 |
| Calcium Silicate | 5.89 | 5.0 |
| Magnesium Stearate | 0.59 | 0.5 |
| Total | 100.0 | 85.0 |

*21.77 mg ziprasidone HCl anhydrous equivalent to 20 mg of ziprasidone free base.

Ziprasidone capsules were prepared according to the procedure set forth in Example 3. The ziprasidone HCl anhydrous had a mean particle size of 135 microns. The ziprasidone capsules were evaluated in a dissolution study as set forth in Example 1. The test results are summarized in Table 1 and FIG. 1.

A dissolution study as described in Comparative Example is performed using the capsules prepared in Example 1, i.e., Geodon® capsules, and the capsules prepared in Example 2-6. A USP Dissolution Apparatus 2 (paddle) was used at 75 rpm containing 900 mL of 0.05 M sodium phosphate monobasic anhydrous buffer containing 2% sodium lauryl sulphate, at pH 7.5 at approximately 37° C.

TABLE 1

Average Dissolved Ziprasidone HCl During a Period of 60 Minutes from Examples 1-6

| Time (min) | Example 1 Dissolved (%) | Example 2 Dissolved (%) | Example 3 Dissolved (%) | Example 4 Dissolved (%) | Example 5 Dissolved (%) | Example 6 Dissolved (%) |
|---|---|---|---|---|---|---|
| 0 | 0 | 0 | 0 | 0 | 0 | 0 |
| 5 | 14.6 | 14.1 | 14.4 | 11.8 | 14.8 | 15.4 |
| 10 | 42.4 | 18.2 | 16.7 | 18.5 | 23.6 | 49.8 |
| 15 | 61.8 | 20.6 | 18.9 | 22.7 | 30.4 | 68.5 |
| 30 | 90.1 | 29.9 | 27.2 | 35.6 | 47.0 | 83.1 |
| 45 | 95.4 | 43.7 | 40.5 | 48.9 | 58.8 | 89.3 |
| 60 | 97.9 | 55.6 | 52.0 | 58.9 | 67.1 | 92.7 |

Referring to the drawing, FIG. 1 is a graph illustrating the average dissolved ziprasidone HCl during a period of 60 minutes for Examples 1-6.

FIG. 1 clearly shows that the dissolution rate of ziprasidone HCl significantly increases with the samples containing a compound having at least one carboxylic acid moiety (Examples 3-6). FIG. 1 also shows that the dissolution rate of ziprasidone HCl is enhanced as the molar ratio of citric acid is increased from 1 to 5 in Examples 3-6, respectively. In addition, FIG. 1 shows that Sample No. 6 which had a molar ratio of citric acid to ziprasidone HCl of 5:1 exhibited an equivalent dissolution profile as compared to commercially-available Geodon® capsules.

EXAMPLE 7

Preparation of Ziprasidone HCl Anhydrous Capsules with 3.3 M Citric Acid.

| Ingredient | Wt. % Composition | mg/Unit |
|---|---|---|
| Ziprasidone HCl Anhydrous | 25.61% | 21.77* |
| Citric Acid | 35.0% | 29.75 |
| Lactose DT Anhydrous | 29.38% | 24.98 |
| Pre-gelatinized Starch | 3.53% | 3.0 |
| Calcium Silicate | 5.89% | 5.0 |
| Magnesium Stearate | 0.59% | 0.50 |
| Total | 100.0% | 85.0 mg |

*21.77 mg ziprasidone HCl anhydrous equivalent to 20 mg of ziprasidone free base Ziprasidone HCl anhydrous having a mean particle size of 135 microns, citric acid, lactose, pre-gelatinized starch, calcium silicate, and 0.29% of magnesium stearate are mixed in a 250 mL beaker for 5 minutes using a spatula to form a pre-mix. The pre-mix is compressed using a mini press to form slugg tablets. The slugg tablets are milled through 0.065" screen equipped with Fitz mill at medium speed setting. To the milled material, 0.30% magnesium stearate is added and mixed for 1 minute. The resulting blend is filled into size 4 hard gelatin capsules. The manufacturing is carried out under a relative humidity of not more than 60%.

EXAMPLE 8

Preparation of Ziprasidone HCl Anhydrous Capsules with 3.3 M Citric Acid.

The ingredients, their composition in terms of weight % (wt.%) and in mg/unit are identical to those of Example 7.

Ziprasidone HCl anhydrous having a mean particle size of 135 microns, citric acid, lactose, pre-gelatinized starch, calcium silicate and 0.29% (wt.%) of magnesium stearate are mixed to form a pre-mix. The pre-mix is compressed using a roller compactor to form slugg tablets. The slugg tablets are milled through 0.065" screen equipped with Fitz mill at medium speed setting. To the milled material, 0.30% (wt.%) of magnesium stearate is added and mixed. The resulting blend is filled into size 4 hard gelatin capsules. The manufacturing is carried out under a relative humidity of not more than 60%.

While the invention has been described with particular reference to certain embodiments thereof, it will be understood that changes and modifications may be made by those of ordinary skill within the scope and spirit of the following claims.

What is claimed is:

1. A pharmaceutical composition having improved solubility comprising ziprasidone hydrochloride anhydrous and a compound having at least one carboxylic acid moiety selected from the group consisting of a monocarboxylic acid, dicarboxylic acid, tricarboxylic acid, tetracarboxylic acid, polycarboxylic acid, and mixtures thereof, wherein the molar ratio of the compound having at least one carboxylic acid moiety to ziprasidone hydrochloride anhydrous is from about 1:1 to about 15:1.

2. A pharmaceutical composition having improved solubility comprising particles of ziprasidone hydrochloride anhydrous and a compound having at least one carboxylic acid moiety, together with one or more pharmaceutically acceptable excipients selected from the group consisting of enteric coating agents, diluents, binders, anti-caking agents, amino acids, fibers, solubilizers, disintegrants, fillers, lubricants, emulsifiers, surfactants, flavorants, solvents, buffers, stabilizers, colorants, dyes, anti-oxidants, anti-adherents, preservatives, electrolytes, glidants, and carrier materials, wherein the molar ratio of the compound having at least one carboxylic acid moiety to the ziprasidone hydrochloride anhydrous is from about 0.1:1 to about 25:1, and said particles have a mean particle size of greater than 85 microns.

3. The composition according to claim 1, wherein the compound having at least one carboxylic acid moiety is selected from the group consisting of ascorbic acid, maleic acid, citric acid, succinic acid, glutaric acid, adipic acid, azelaic acid, sebacic acid, fumaric acid, maleic acid, itaconic acid, 1,3-cyclohexane dicarboxylic acid, 1,4-cyclohexanedicarboxylic acid, diglycolic acid, 2,5-norbomanedicarboxylic acid, phthalic acid, terephthalic acid, 1,4-naphthalenedicarboxylic acid, 2,5-naphthalenedicarboxylic acid, diphenic acid, 4,4'-oxydibenzoic acid, 4,4'-sulfonyldibenzoic acid and isophthalic acid, and mixtures thereof.

4. The composition according to claim 3, wherein the compound having at least one carboxylic acid moiety is selected from the group consisting of ascorbic acid, maleic acid, and citric acid.

5. The composition according to claim 4, wherein the compound having at least one carboxylic acid moiety is citric acid.

6. The composition according to claim 1, wherein the molar ratio of the compound having at least one carboxylic acid moiety to ziprasidone hydrochloride anhydrous is from about 2:1 to about 10:1.

7. The composition according to claim 6, wherein the molar ratio of the compound having at least one carboxylic acid moiety to ziprasidone hydrochloride anhydrous is about 3.5:1 to about 4:1.

8. The composition according to claim 1, which additionally comprises at least one excipient.

9. The composition according to claim 8, wherein the excipient is selected from the group consisting of enteric coating agents, diluents, binders, anti-caking agents, amino acids, fibers, solubilizers, disintegrants, fillers, lubricants, emulsifiers, surfactants, flavorants, solvents, buffers, stabilizers, colorants, dyes, anti-oxidants, anti-adherents, preservatives, electrolytes, glidants, carrier materials, and combinations thereof.

10. The composition according to claim 1, which is in the form selected from the group consisting of a tablet, granules, bar, block, disc, capsule, caplet and powder.

11. The composition according to claim 10, which is in the form of a capsule.

12. The composition according to claim 1, wherein the ziprasidone hydrochloride anhydrous has a mean particle size of at least about 85 microns and the molar ratio is from about 1:1 to 5:1.

13. A wet granulation method of preparing a pharmaceutical composition having improved solubility comprising ziprasidone hydrochloride anhydrous and a compound having at least one carboxylic acid moiety, wherein the molar ratio of the compound having at least one carboxylic acid moiety to ziprasidone hydrochloride anhydrous is from about 0.1:1 to about 25:1, said method comprising:
   (a) combining a compound having at least one carboxylic acid moiety with ziprasidone hydrochloride anhydrous and, optionally, one or more excipients, to form a premix;
   (b) adding a solvent and, optionally, a surfactant, to the premix formed in step
   (a) to form a wet granulation; and
   (c) drying the wet granulation to form a pharmaceutical composition.

14. A method of preparing a pharmaceutical composition having improved solubility comprising ziprasidone hydrochloride anhydrous and a compound having at least one carboxylic acid moiety, wherein the molar ratio of the compound having at least one carboxylic acid moiety to ziprasidone hydrochloride anhydrous is from about 0.1:1 to about 25:1, said method comprising:
   (a) combining ziprasidone hydrochloride anhydrous and, optionally, one or more excipients to form a premix;
   (b) adding a mixture comprising a solvent and a compound having at least one carboxylic acid moiety to the premix formed in step (a) to form a wet granulation; and
   (c) drying the wet granulation to form a pharmaceutical composition.

15. A dry compaction method of preparing a pharmaceutical composition having improved solubility comprising ziprasidone hydrochloride anhydrous and a compound having at least one carboxylic acid moiety, wherein the molar ratio of the compound having at least one carboxylic acid moiety to ziprasidone hydrochloride anhydrous is from about 0.1:1 to about 25:1, said method comprising:
   (a) combining a compound having at least one carboxylic acid moiety with ziprasidone hydrochloride anhydrous and, optionally, one or more excipients, to form a premix;
   (b) compacting the premix formed in step (a), optionally in the presence of one or more excipients, to form an agglomerate; and
   (c) breaking the agglomerate formed in step, optionally in the presence of one or more excipients, to form a pharmaceutical composition.

16. A method for treating schizophrenia in a patient comprising administering an effective amount of a pharmaceutical composition to said patient, said composition comprising ziprasidone hydrochloride anhydrous and a compound having at least one carboxylic acid moiety, wherein the molar ratio of the compound having at least one carboxylic acid moiety to ziprasidone hydrochloride anhydrous is from about 0.1:1 to about 25:1.

17. A pharmaceutical composition comprising ziprasidone hydrochloride anhydrous and citric acid, wherein the molar ratio of citric acid to ziprasidone hydrochloride anhydrous is from about 1:1 to about 15:1.

18. The pharmaceutical composition of claim 17, wherein the molar ratio of citric acid to ziprasidone hydrochloride anhydrous is about 5:1.

19. The pharmaceutical composition of claim 18, wherein the molar ratio of citric acid to ziprasidone hydrochloride anhydrous is from about 3.5:1 to about 4:1.

20. The composition according to claim 17, further comprising at least one excipient.

21. The composition according to claim 20, wherein the excipient is selected from the group consisting of enteric coating agents, diluents, binders, anti-caking agents, amino acids, fibers, solubilizers, disintegrants, fillers, lubricants, emulsifiers, surfactants, flavorants, solvents, buffers, stabilizers, colorants, dyes, anti-oxidants, anti-adherents, preservatives, electrolytes, glidants, carrier materials, and combinations thereof.

22. The composition according to claim 17, which is in the form of a solid material selected from the group consisting of a tablet, granules, bar, block, disc, capsule, caplet and powder.

23. The composition according to claim 22, which is in the form of a capsule.

24. The composition according to claim 2, wherein the compound having at least one carboxylic acid moiety is selected from the group consisting of ascorbic acid, maleic acid, citric acid, and combinations thereof 25. The composition according to claim 24, wherein the compound comprises citric acid.

26. The composition according to claim 24, wherein the molar ratio of the compound having at least one carboxylic acid moiety to ziprasidone hydrochloride anhydrous is from about 1:1 to 5:1.

27. The composition according to claim 26, wherein the molar ratio of the compound having at least one carboxylic acid moiety to ziprasidone hydrochloride anhydrous is about 5:1.

28. The composition according to claim 2, wherein the molar ratio of the compound having at least one carboxylic acid moiety to ziprasidone hydrochloride anhydrous is from about 1:1 to 5:1.

29. The composition of claim 24, wherein the compound comprises citric acid and the molar ratio of the compound having at least one carboxylic acid moiety to ziprasidone hydrochloride anhydrous is from about 1:1 to 5:1.

30. The composition of claim 29, wherein the molar ratio of the compound having at least one carboxylic acid moiety to ziprasidone hydrochloride anhydrous is about 5:1.

* * * * *